(12) United States Patent
Yamazaki et al.

(10) Patent No.: US 9,314,794 B2
(45) Date of Patent: Apr. 19, 2016

(54) NEEDLE PORT

(71) Applicant: Shimadzu Corporation, Kyoto-Shi (JP)

(72) Inventors: Tomoyuki Yamazaki, Kyoto (JP); Przemyslaw Stasica, Hertfordshire (GB); Bob Boughtflower, Hertfordshire (GB)

(73) Assignee: Shimadzu Corporation, Kyoto (JP)

( * ) Notice: Subject to any disclaimer, the term of this patent is extended or adjusted under 35 U.S.C. 154(b) by 100 days.

(21) Appl. No.: 13/874,178

(22) Filed: Apr. 30, 2013

(65) Prior Publication Data

US 2013/0309146 A1 Nov. 21, 2013

(30) Foreign Application Priority Data

May 15, 2012 (JP) .................................. 2012-111175

(51) Int. Cl.
| | |
|---|---|
| *B01D 15/14* | (2006.01) |
| *G01N 30/18* | (2006.01) |
| *B01L 3/00* | (2006.01) |

(Continued)

(52) U.S. Cl.
CPC ............ *B01L 3/563* (2013.01); *G01N 35/1011* (2013.01); *B01L 3/565* (2013.01); *G01N 30/16* (2013.01)

(58) Field of Classification Search
CPC ........ B01D 15/10; B01D 15/14; G01N 30/04; G01N 30/16; G01N 30/18; G01N 30/20
USPC ..................... 422/70, 89, 546; 95/89; 96/105; 73/23.41, 61.55
See application file for complete search history.

(56) References Cited

U.S. PATENT DOCUMENTS

| | | |
|---|---|---|
| 2006/0213258 A1 | 9/2006 | Hale et al. |
| 2008/0314412 A1* | 12/2008 | Grippo et al. .............. 134/22.11 |
| 2012/0164026 A1* | 6/2012 | Dehmer et al. ............. 422/68.1 |

(Continued)

FOREIGN PATENT DOCUMENTS

| | | |
|---|---|---|
| EP | 2336764 A1 | 6/2011 |
| GB | 2486677 A | 6/2012 |

(Continued)

OTHER PUBLICATIONS

Examination Report received for Chinese Patent Application No. 201310177922.5 mailed on Jun. 23, 2014, 7 pages (2 pages of English Translation and 5 pages of Office Action).

(Continued)

*Primary Examiner* — Jan Ludlow
(74) *Attorney, Agent, or Firm* — Morgan, Lewis & Bockius LLP

(57) ABSTRACT

A liquid leakage between a needle and a needle port is prevented. To this end, a guide section, a passage section, and a tapered section are provided in an in-port path of a needle port. The guide section has an inside diameter larger than the outside diameter of a body of a needle. The passage section has an inside diameter smaller than the outside diameter of the body of the needle and larger than the tip diameter of a tapered portion of the needle. The tapered section connects the guide section and the passage section. The taper angle θ2 of the tapered section is set to be larger than the taper angle θ1 of the tapered portion of the needle, and the width w of the tapered section is set to be smaller than half the difference between the outside diameter of the body and the tip diameter of the needle.

2 Claims, 5 Drawing Sheets

(51) Int. Cl.
*G01N 35/10* (2006.01)
*G01N 30/16* (2006.01)

(56) References Cited

U.S. PATENT DOCUMENTS

2013/0008237 A1* 1/2013 Usowicz et al. ............. 73/61.52
2013/0049302 A1* 2/2013 Lemelin et al. ............... 277/345

FOREIGN PATENT DOCUMENTS

JP 2003-149217 5/2003
WO WO 2009/044427 A1 4/2009

OTHER PUBLICATIONS

United Kingdom Office Action mailed Nov. 28, 2013 for corresponding United Kingdom Patent App. No. 1307755.7.

* cited by examiner

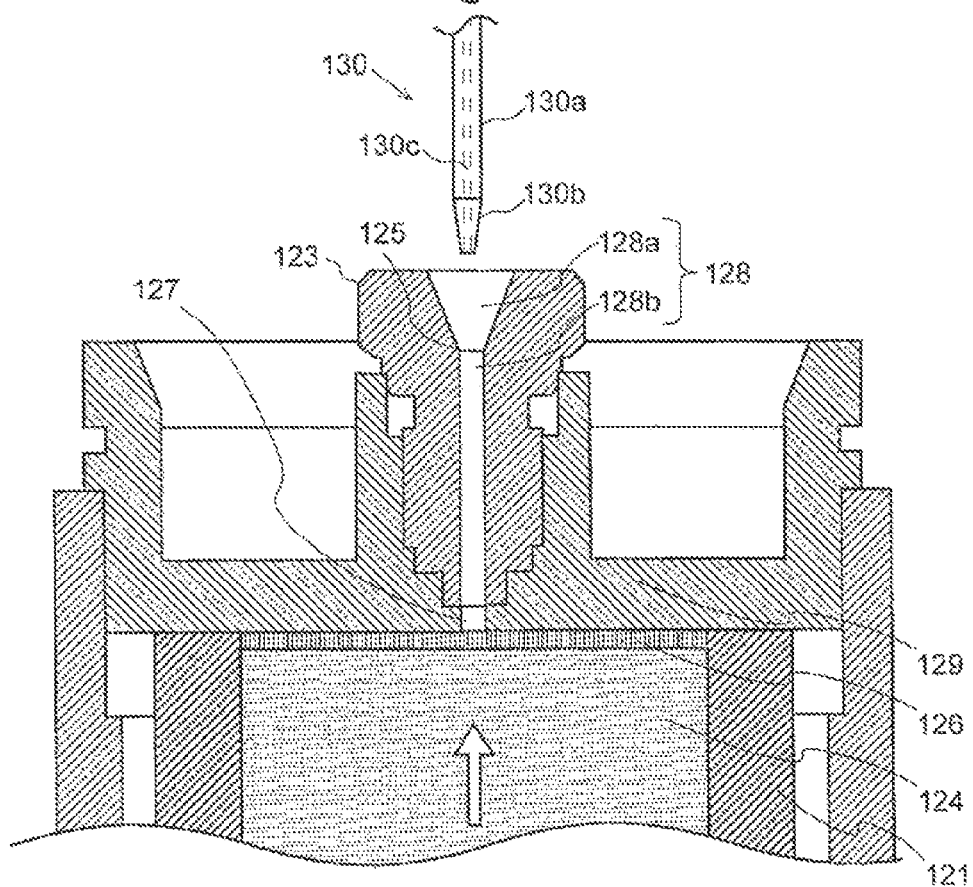

NEEDLE PORT

TECHNICAL FIELD

The present invention relates to a needle port which is provided in a trap column or other part of a preparative separation-purification system.

BACKGROUND ART

In the pharmaceutical industry, for example, and other fields, preparative separation-purification systems utilizing a liquid chromatograph are used to collect samples of a variety of chemically synthesized compounds in order to store those samples in a library or analyze them in more detail. Conventional examples of the preparative separation-purification system are disclosed in Patent Documents 1 and 2.

In those conventional apparatuses, target components are collected from a sample solution as follows. First, target components (compounds) in a sample solution are temporally separated by a liquid chromatograph. The separated target components are then respectively introduced into different trap columns and temporarily captured therein. Subsequently, a solvent is supplied into each trap column to elute the component from the trap column and collect it in a container. Thus, a plurality of eluates each containing a target component at a high concentration are respectively collected in a plurality of containers. These separately collected solutions are then subjected to a vaporizing and drying process to remove the solvent and collect the target components in solid form.

Such preparative separation-purification systems include a connection mechanism, in which a needle and a needle port are used, in order to place a trap column in the liquid passage. A needle includes a passage through which a liquid passes. A pipe for introducing a liquid or a pipe for disposing a liquid is connected to the base (the end opposite the tip) of the needle. A needle port is attached to the outlet end and the inlet end of the trap column respectively. A path (in-port path) for allowing a liquid to pass through is formed inside the needle port. When a trap column is placed in the liquid passage, the tip of the needle attached to the liquid introducing pipe is inserted into the needle port at the inlet end, and the tip of the needle attached to the liquid disposing pipe is inserted into the needle port at the outlet end. This establishes a liquid-tight connection between the path within each needle and the in-port path within each needle port, thus allowing a liquid to flow through the trap column.

The connection between the needle and the needle port is now described in detail with reference to FIG. 6. Although FIG. 6 shows the configuration around the outlet end of the trap column for the sake of simplicity, the configuration around the inlet end is basically the same.

The trap column 121 has a hollow cylindrical shape, and its internal space 124 is filled with a granular filler. A mesh cap 126 for preventing the filler from leaking and a cap 129 are provided at the end of the trap column 121. An aperture 127 for allowing a liquid to pass through is formed in the cap 129. A cavity is formed outside the aperture 127, and the needle port 123 is fixed with the cavity. When the needle port 123 is fixed with the cavity, the in-port path 128 communicates with the aperture 127. The in-port path 128 has a funnel-shape, and is composed of an outer tapered section 128a and a straight passage section 128b. A needle 130 has a tapered portion 130b at the tip of a straight body 130a, and a path 130c is formed inside the needle 130.

When the tip of the needle 130 is inserted into the in-port path 128 of the needle port 123, the tapered portion 130b is tightly attached to a mouth 125 of the passage section 128b. This establishes a liquid-tight connection between the path 130c in the needle 130 and the in-port path 128.

BACKGROUND ART DOCUMENT

Patent Documents

[Patent Document 1] WO-A 2009/044427
[Patent Document 2] JP-A 2003-149217

DISCLOSURE OF THE INVENTION

Problem to be Solved by the Invention

In order to automatically separate and collect many samples, the needle 130 as previously described is usually driven by a motor or other machines. Although such a driving mechanism is designed to operate with precision, the central axis of the needle 130 and that of the needle port 123 might not be exactly aligned when the needle 130 is inserted into the needle port 123 because of, for example, a slight mis-placement of the trap column 121 or other reasons. The provision of the tapered section 128a of the needle port 123 ensures that the needle 130 is correctly guided to the passage section 128b. However, in doing so, the tip of the needle 130 touches the tapered section 128a, and the surface of the tapered section 128a is scratched as the needle 130 is pushed down. Such a scratch near the mouth 125 of the passage section 128b impedes an adequately tight attachment between the tapered portion 130b of the needle 130 and the mouth 125. This causes liquid leakage through the gap therebetween.

The aforementioned problem may occur not only in the needle port provided in the trap column as described above, but also in the needle port provided in an analysis column, in an injection port, or in other similar units. In addition, this problem may occur not only in the needle port provided in a preparative separation-purification system, but also in a needle port provided in a same or similar unit of a liquid chromatograph apparatus, an auto sampler, or other apparatuses.

The present invention has been achieved to solve the aforementioned problem, and the main objective thereof is to provide a needle port which can assuredly prevent the occurrence of a liquid leakage from the connection section between the needle and the needle port.

Means for Solving the Problem

To solve the aforementioned problem, the present invention provides a needle port having an in-port path into which a needle is to be inserted, the needle having a tapered portion on an end of a body and a path inside the body through which a liquid passes, wherein the in-port path includes:

a) a guide section having an inside diameter larger than an outside diameter of the body of the needle;

b) a passage section having an inside diameter smaller than the outside diameter of the body of the needle and larger than a tip diameter of the tapered portion of the needle; and c) a tapered section for connecting the guide section and the passage section, the tapered section having a taper angle larger than a taper angle of the tapered portion of the needle and the tapered section having a width smaller than half a difference between the outside diameter of the body of the needle and the tip diameter.

The taper angle is the angle formed between a tapered surface and the central axis of the circular cone formed by extending the tapered surface. The width of the tapered section is half the difference between the diameters at both ends of the tapered section (i.e. the difference between the largest inside diameter and the smallest inside diameter).

Hereinafter, the configuration of the needle port according to the present invention is described with reference to FIGS. 1A through 1C. It should be noted that FIGS. 1A through 1C are merely conceptual diagrams for clear explanation of the present invention, and do not limit the configuration of the present invention.

In the needle port according to the present invention, as shown in FIG. 1A, $\phi a$ denotes the outside diameter of the body 31a of the needle 31, $\phi b$ denotes the tip diameter of the tapered portion 31b of the needle 31, $\phi c$ denotes the inside diameter of the guide section 62 of the in-port path 60, and $\phi d$ denotes the inside diameter of the passage section 64. The taper angle of the tapered portion 31b of the needle 31 is denoted by $\theta a$, and the taper angle of the tapered section 63 of the in-port path 60 is denoted by $\theta b$.

To connect the needle to the needle port according to the present invention, first, the needle 31 is moved downward from above the needle port toward the in-port path 60. In this process, as shown in FIG. 1A, even if the axes of the needle 31 and the needle port are misaligned, as long as the circumference of the tip of the tapered portion 31b of the needle 31 is situated within the inner circumference of the guide section 62, the tapered portion 31b and the body 31a of the needle 31 are guided by the inner surface of the guide section 62 and the needle 31 is moved down.

When the needle 31 is further moved down and the tip of the needle 31 arrives at the tapered section 63 of the in-port path 60, with the needle port according to the present invention, the tip of the tapered portion 31b does not come into contact with the inner peripheral surface of the tapered section 63, as shown in FIG. 1B. This is because the width x of the tapered section 63 of the in-port path 60 is smaller than half the difference between the outside diameter $\phi a$ of the body 31a and the tip diameter $\phi b$ of the tapered portion 31b of the needle 31 ($x<[(\phi a-\phi b)/2]$), and the taper angle of the tapered portion 31b of the needle 31 is smaller than that of the tapered section 63 of the in-port path 60 ($\theta a<\theta b$).

Then, when the needle 31 is further moved down, a part of the outer peripheral surface of the tapered portion 31b of the needle 31 comes into contact with a part of the inner peripheral surface of the tapered section 63 of the in-port path 60. Hence, the needle 31 is guided and the misalignment between the axes of the needle and the needle port is corrected. Finally, as shown in FIG. 1C, the tapered portion 31b of the needle 31 seals a mouth 65 of the passage section 64 of the in-port path 60.

As described above, with the needle port according to the present invention, even if the axes of the needle and the needle port are misaligned, the misalignment will be corrected and the tip of the needle will not damage the tapered section of the needle port. Therefore, the liquid-tightness between the needle and the needle port can be always assured.

In order to allow the needle to be inserted into the needle port even in the case where there is a larger misalignment between the axes of the needle and the needle port, it is preferable to provide a tapered inlet section before the guide section of the in-port path. When the tip of the tapered portion of the needle comes into contact with the inlet section, its surface may be scratched. However, this will not cause any problems because the inlet section does not influence the liquid-tightness between the needle port and the needle.

The present invention can be applied to a needle port in various systems, such as a preparative separation-purification system, a liquid chromatograph apparatus, an auto sampler, or other apparatuses in which a needle is used for providing a liquid to a passage or for changing passages. In particular, the present invention can be applied to an inlet/outlet end of a variety of columns, an injection port, and other similar units provided in such systems.

Effects of the Invention

In the needle port according to the present invention, the dimensions and angles of the relevant sections are appropriately set. Hence, even in the case where the needle is inserted into the needle port while their axes are misaligned, the tip of the tapered portion of the needle will not come into contact with the tapered section of the in-port path. Hence, unlike conventional needle ports, the surface of the tapered section will not be scratched, which can always assure the liquid-tightness between the needle and the needle port.

BRIEF DESCRIPTION OF THE DRAWINGS

FIG. 6 is a magnified vertical sectional view of a trap column having a conventional needle port.

BEST MODES FOR CARRYING OUT THE INVENTION

Figure 1A:
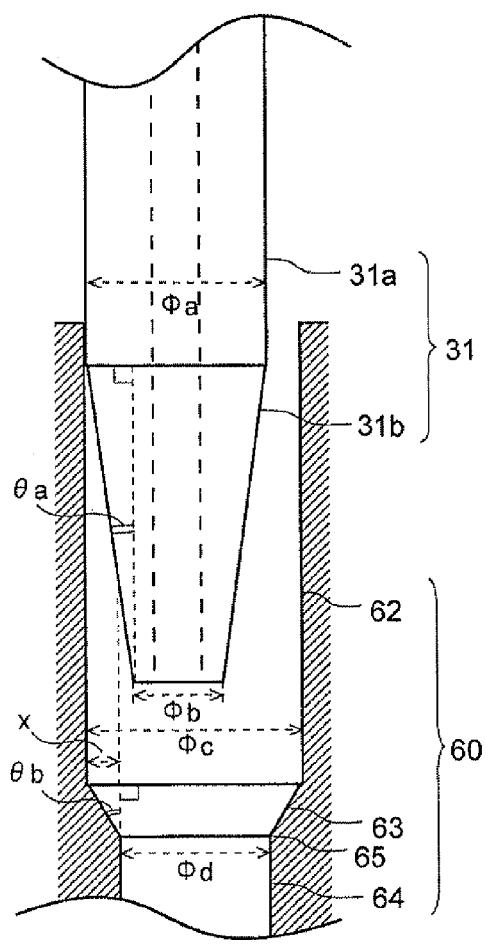
FIGS. 1A through 1C are conceptual diagrams showing the configuration of a needle port according to the present invention.
Figure 1B:
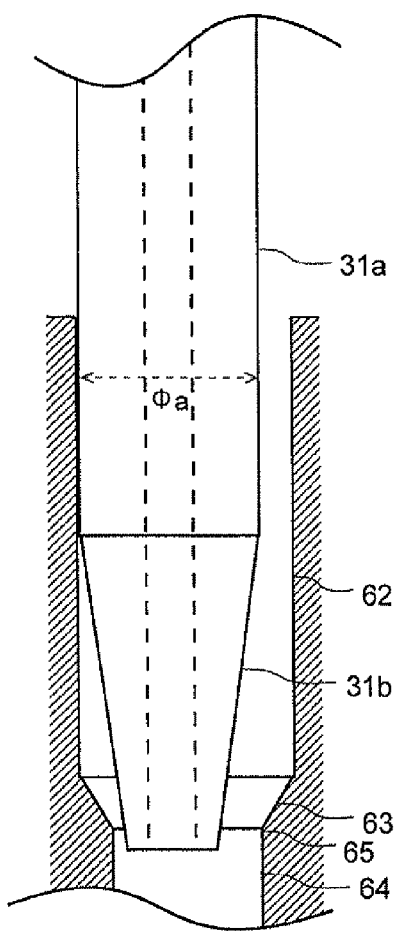
Figure 1C:
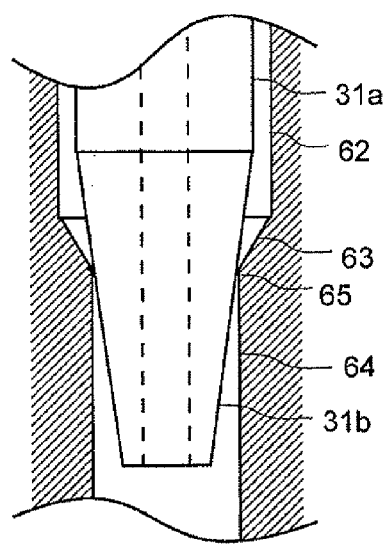
Figure 2:
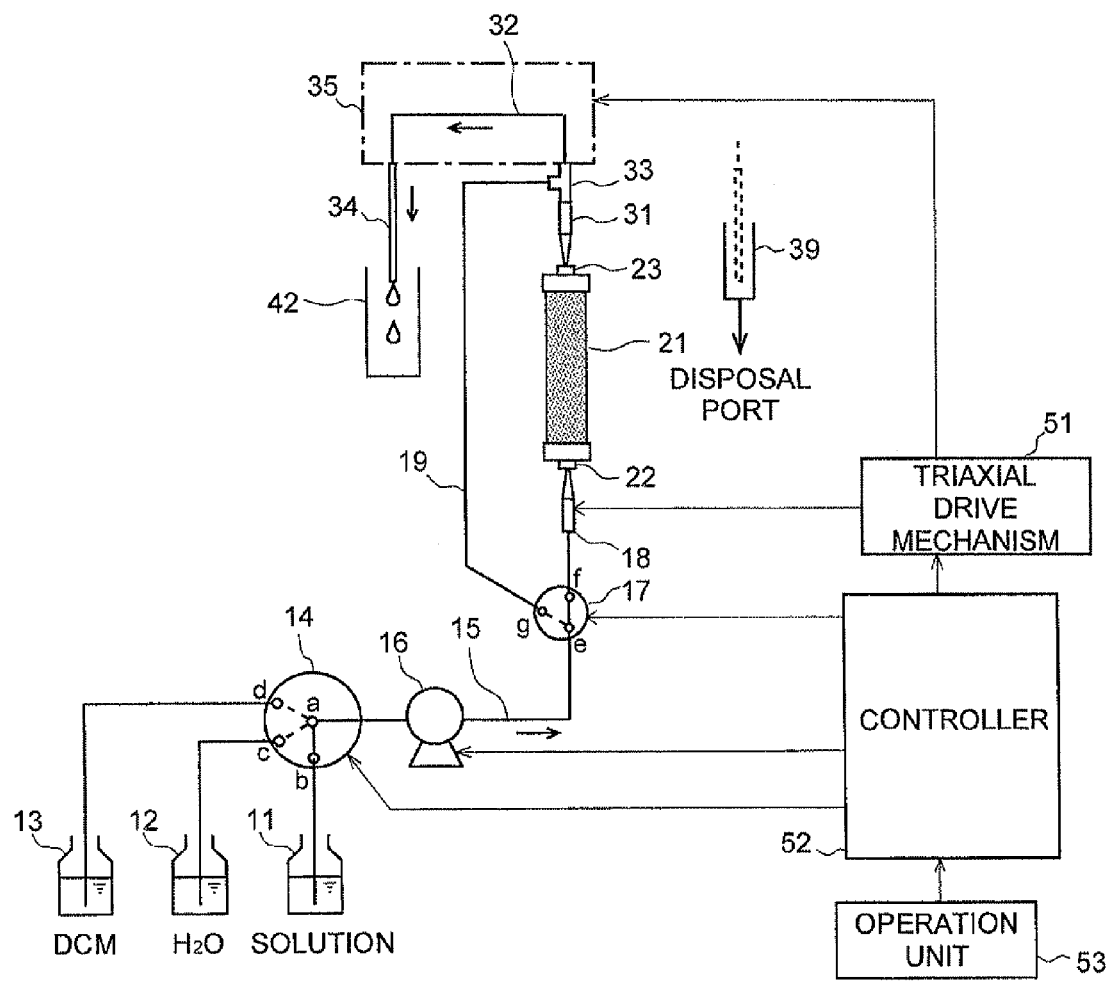
FIG. 2 is a block configuration diagram illustrating the main components of a preparative separation-purification system having a needle port according to an embodiment of the present invention.
Figure 3:
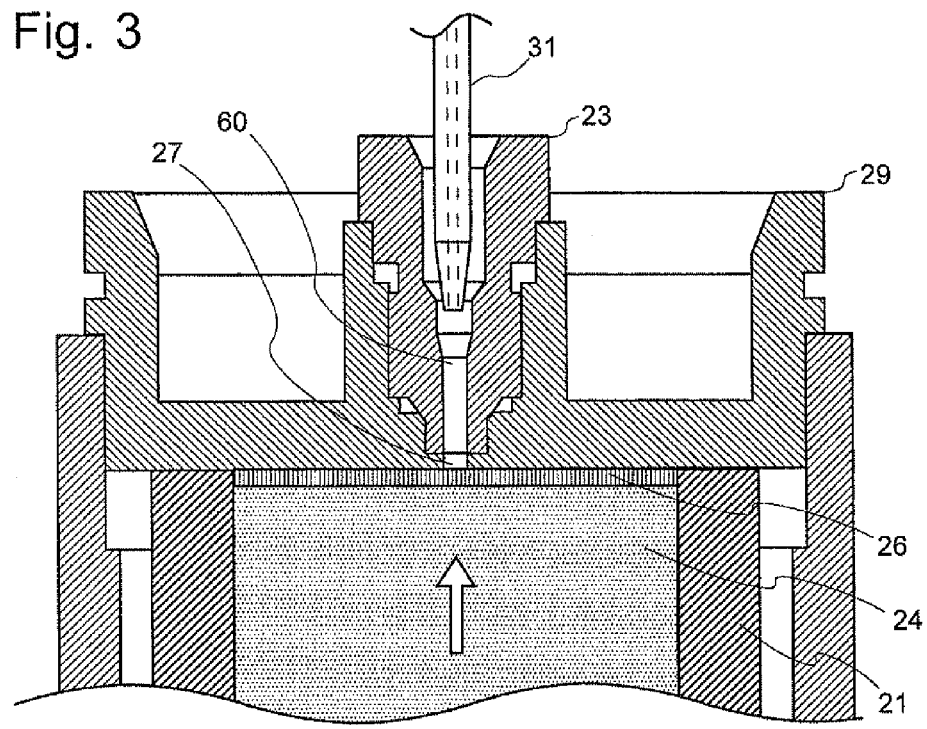
FIG. 3 is a magnified vertical sectional view of a trap column according to the present embodiment.

A preparative separation-purification system which uses the needle port according to the present invention is described in detail with reference to FIGS. 2, 3, 4A, 4B, 5A, 5B, and 5C. FIG. 2 is a block configuration diagram illustrating the main components of the preparative separation-purification system having a trap column which includes the needle port of an embodiment of the present invention.

The preparative separation-purification system is for collecting a target component in a solution which contains the target component in a trap column 21, and purifying and obtaining it in a solid form. The needle ports 22 and 23 according to the present invention are respectively attached to the inlet end and the outlet end of the trap column 21 which is provided in this preparative separation-purification system. The same basic configuration is shared by both needle ports 22 and 23.

Containers 11, 12, and 13 hold, respectively, a solution which contains the target component, pure water which is used as a cleaning liquid for the trap column 21, and dichloromethane which acts as an eluting solvent. A passage selector valve 14 and a supply pump 16 are provided to sequentially collect the target component, rinse the trap column 21, and elute the target component by supplying one of the liquids contained in the containers 11, 12, and 13 to an introduction passage 15 so as to selectively deliver it into the trap column 21. A two-way selector valve 17 is provided on the introduction passage 15 so as to change the passage configuration so that the selected liquid is selectively supplied to either a needle 18 or a dilution passage 19. The other end of the dilution passage 19 is connected to a discharge passage 32 at a downstream of the trap column 21 by way of a T-joint 33. This allows a liquid (i.e. dilution liquid) which passes through the dilution passage 19 to flow into the discharge passage 32. The needle 18 can be moved by means of a triaxial drive mechanism 51.

A needle 31 is provided at the upstream end of the discharge passage 32. The needle 31, the discharge passage 32 and a discharge nozzle 34 which will be described later are attached to a fraction collector head 35. The fraction collector head 35 can be moved by means of the triaxial drive mechanism 51. Moving and connecting the needles 18 and 31 to the inlet end and the outlet end of the trap column 21, respectively, allows the liquid drawn by the supply pump 16 to be introduced into the trap column 21 through the introduction passage 15, and allows the liquid which has passed through the trap column 21 to be discharged to the discharge passage 32. The discharge nozzle 34 is attached to the downstream end of the discharge passage 32. By moving the fraction collector head 35 to which the discharge nozzle 34 is attached by means of the triaxial drive mechanism 51, the liquid discharged from the trap column 21 to the discharge passage 32 can be collected in a collection container 42 through the discharge nozzle 34 or discharged to a disposal port 39 which is placed in the moving range of the fraction collector head 35 by means of the triaxial drive mechanism 51.

A controller 52 which includes a CPU and other units controls, in accordance with a previously set program, the selecting operation of the selector valves 14 and 17, the driving operation of the triaxial drive mechanism 51, the operation of the supply pump 16 (flow rate and/or flow speed), and other operations to perform a preparative separation-purification operation. The conditions for the preparative separation-purification operation and other information are input and set through an operation unit 53.

As previously described, the trap column 21 for collecting a target component is provided in the preparative separation-purification system. The needle ports 22 and 23 according to the present embodiment are attached to the inlet end and the outlet end of the trap column 21, respectively. Hereinafter, the configuration of these units is described hereinafter in detail with reference to FIGS. 3, 4A, and 4B.

The trap column 21 has a hollow cylindrical shape, and its internal space 24 is filled with a granular filler. A mesh cap 26 for preventing the filler from leaking and a cap 29 are provided at the end of the trap column 21. An aperture 27 for allowing a liquid to pass through is formed in the cap 29. A cavity is formed outside the aperture 27, and the needle port 23 is fixed with the cavity. When the needle port 23 is fixed with the cavity, the in-port path 60 of the needle port 23 communicates with the aperture 27.

A tapered portion 31b is provided at an end of a straight body 31a of the needle 31. In addition, a path 31c through which a liquid passes is formed inside the needle 31. An in-port path 60 is composed of in external to internal order, an inlet section 61, a guide section 62, a tapered section 63, and a passage section 64. Among these, the guide section 62 and the passage section 64 have a straight shape, while the diameters of the inlet section 61 and the tapered section 63 become narrower in the insertion direction of the needle 31.

Figure 4A:
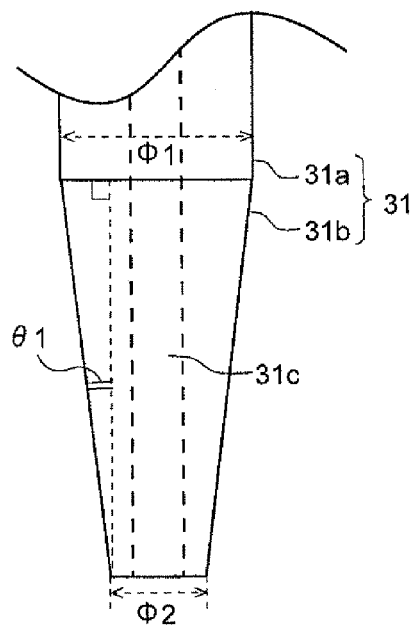
FIG. 4A is a magnified view showing the portion around the tip of a needle according to the present embodiment.
Figure 4B:
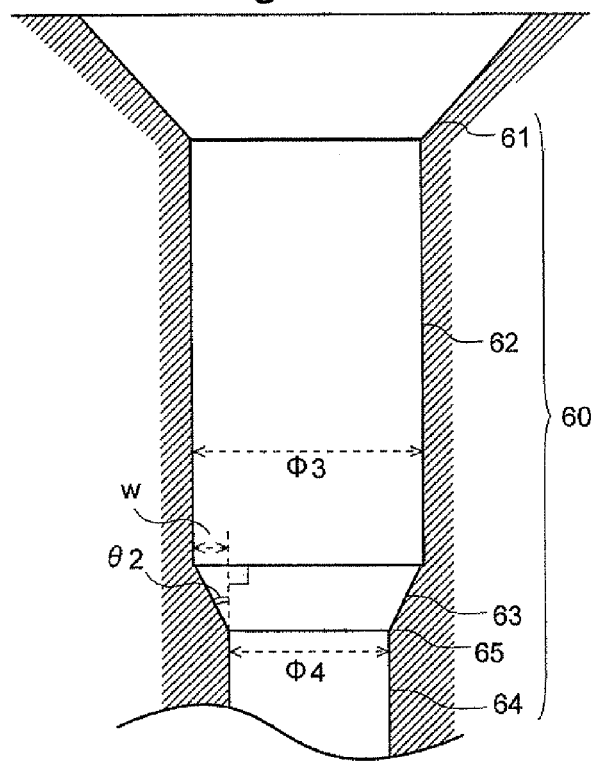
FIG. 4B is a magnified vertical sectional view of an in-port path of the needle port according to the present embodiment.

The dimensions and angles of each portion in the needle ports 22 and 23 according to the present embodiment are now described. As shown in FIGS. 4A and 4B, the outside diameter of the body 31a of the needle 31 is denoted by $\phi 1$, the tip diameter of the tapered portion 31b of the needle 31 is denoted by $\phi 2$, the inside diameter of the guide section 62 of the in-port path 60 is denoted by $\phi 3$, and the inside diameter of the passage section 64 is denoted by $\phi 4$. The taper angle of the tapered portion 31b of the needle 31 is denoted by $\theta 1$, the taper angle of the tapered section 63 of the in-port path 60 is denoted by $\theta 2$, and the width of the tapered section 63 of the in-port path 60 is denoted by w.

In the needle ports 22 and 23 according to the present embodiment, $\phi 1$, $\phi 2$, $\phi 3$, and $\phi 4$ are 2.1 mm, 1.25 mm, 2.20 mm, and 1.4 mm, respectively. The width w is 0.4 mm. The taper angles $\theta 1$ and $\theta 2$ are 15 degrees and 60 degrees, respectively. The taper angle of the inlet section 61 is 60 degrees. The entire length of the in-port path 60 is 11.7 mm. The longitudinal lengths of the inlet section 61, the guide section 62, the tapered section 63, and the passage section 64 are 1 mm, 4.2 mm, 0.7 mm, and 5.8 mm, respectively.

The dimensions and angles of the portions which are indicated above are not limited to the aforementioned values, and can be appropriately changed within the following conditions. The inside diameter $\phi 3$ of the guide section 62 of the in-port path 60 is set to be larger than the outside diameter $\phi 1$ of the body 31a of the needle 31, and the width w of the tapered section 63 of the in-port path 60 is set to be smaller than half the difference between the outside diameter $\phi 1$ of the body 31a of the needle 31 and the tip diameter $\phi 2$ of the tapered portion 31b (w<[($\phi 1-\phi 2$)/2]). In addition, the taper angle of the tapered portion 31b of the needle 31 is set to be smaller than that of the tapered section 63 of the in-port path 60 ($\theta 1<\theta 2$). Further, the smallest inside diameter of the inlet section 61 is set to be the same as the inside diameter of the guide section 62.

The operation of the preparative separation-purification system which has the needle port of the present embodiment is now described. First, the controller 52 moves the needle 18 and the fraction collector head 35 by means of the triaxial drive mechanism 51 so as to insert the tip of the needle 18 into the needle port 22 of the inlet end of the trap column 21, and to insert the tip of the needle 31 into the needle port 23 of the outlet end. Consequently, the introduction passage 15 and the discharge passage 32 are connected to the trap column 21. The discharge nozzle 34 is inserted into the disposal port 39.

Hereinafter, the operation of inserting the tip of the needle 31 into the needle port 23 provided at the outlet end of the trap column 21 is described with reference to FIGS. 5A through 5C. The operation of inserting the tip of the needle 18 into the needle port 22 of the inlet end of the trap column 21 is performed in the same manner as is described below, except that the operations are vertically inverted.

Figure 5A:
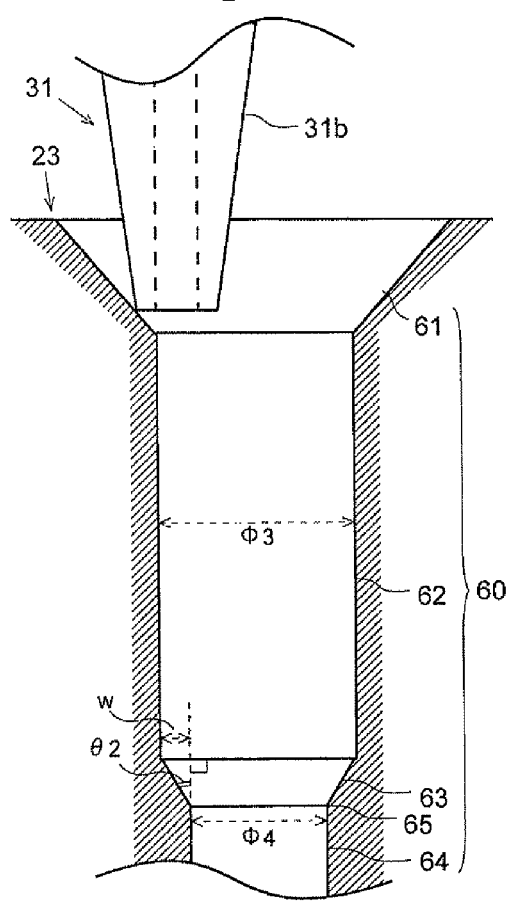
FIGS. 5A through 5C are schematic diagrams showing how a needle is inserted into the needle port according to the present embodiment.
Figure 5B:
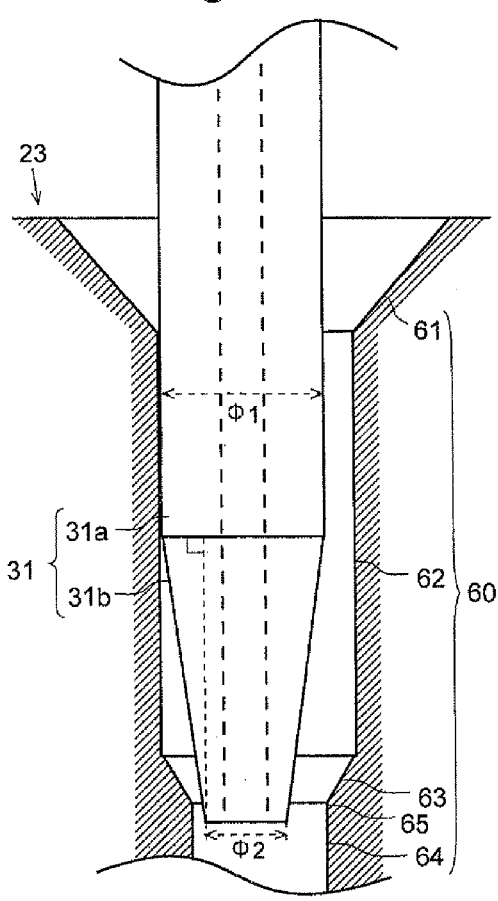
Figure 5C:
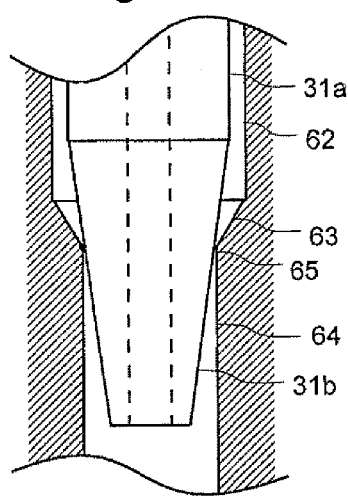

In the case where the axes of the needle 31 and the needle port 23 are misaligned as shown in FIG. 5A, when the needle 31 goes down to the needle port 23, the tip of the tapered portion 31b of the needle 31 comes into contact with the inner peripheral surface of the inlet section 61 of the in-port path 60. Then, the tip of the tapered portion 31b of the needle 31 is guided by the tapered inner peripheral surface of the inlet section 61 and reaches the inlet of the guide section 62. After reaching the guide section 62, the needle 31 moves down as its body 31a is guided by the inner peripheral surface of the guide section 62.

When the needle 31 further moves down, the tip of the tapered portion 31b of the needle 31 reaches the tapered section 63 of the in-port path 60. With the needle port 23 according to the present embodiment, as shown in FIG. 5B, the tip of the tapered portion 31b does not come into contact with the inner peripheral surface of the tapered section 63. This is because, as previously described, the width w of the tapered section 63 of the in-port path 60 is smaller than half the difference between the outside diameter $\phi1$ of the body 31a and the tip diameter $\phi2$ of the tapered portion 31b of the needle 31 ($w<[(\phi1-\phi2)/2]$), and the taper angle of the tapered portion 31b of the needle 31 is smaller than that of the tapered section 63 of the in-port path 60 ($\theta1<\theta2$).

When the needle 31 further moves down, a portion of the outer peripheral surface of the tapered portion 31b of the needle 31 comes into contact with a portion of the inner peripheral surface of the tapered section 63 of the in-port path 60. In this state, as the needle 31 further moves down, the misalignment between the axes of the needle 31 and the needle port 23 is corrected. Finally, as shown in FIG. 5C, the tapered portion 31b of the needle 31 seals the mouth 65 of the passage section 64, and the needle 31 is connected to the needle port 23.

In the needle port 23 of the present embodiment, the inlet section 61 is provided before the guide section 62 so as to correct a significant misalignment of the needle 31. However, if the triaxial drive mechanism 51 is accurate, the inlet section 61 can be omitted.

After the needles 18 and 31 are respectively connected to the needle ports 22 and 23 of the net end and the outlet end of the trap column 21 as previously described, the controller 52 first controls the selecting operation of the selector valves 14 and 17 and the operation of the supply pump 16 so as to introduce the solution contained in the container 11 and contains the target component into the trap column 21 and to dispose the liquid discharged from the trap column 21 to the disposal port 39 via the discharge passage 32 and the discharge nozzle 34. In this manner, the target component is collected in the trap column 21. Then, the controller 52 controls the relevant units in order to introduce the pure water contained in the container 12 into the trap column 21 so as to rinse the trap column 21 and remove undesired substances, such as salts, and to dispose of the used pure water, which is discharged from the trap column 21 into the disposal port 39 in the same way as the aforementioned solution.

To collect the target component from the trap column 21, the controller 52 controls the relevant units as follows. The discharge nozzle 34 is pulled off from the disposal port 39 and inserted into the collection container 42 while dichloromethane contained in the container 13 is introduced into the trap column 21. Then, the liquid containing the target component at high concentration and discharged from the outlet end of the column 21 is collected in the collection container 42 via the discharge passage 32 and the discharge nozzle 34. In this operation, during a predetermined time period from the point in time when the eluting solvent starts to be discharged from the outlet end of the trap column 21, the controller 52 controls the selector valve 17 so as to intermittently change the passage from the needle 18 side (port f) to the dilution passage 19 side (port g), so that dichloromethane drawn by the supply pump 16 is directly sent to the discharge passage 32 without passing through the trap column 21. As a result, the liquid containing the target component at high concentration is diluted, which makes it difficult for the deposition of the target component to occur in the discharge passage 32. After that, the liquid collected in the collection container 42 may be vacuum-dried or processed appropriately to obtain the target component in a solid form.

As described above, with the needle ports 22 and 23 according to the present embodiment, the dimensions and angles of their portions are appropriately set. Hence, even in the case where the needle (18 or 31) is inserted into the needle port (22 or 23) while the axes between the needle (18 or 31) and the needle port (22 or 23) are misaligned, the tip of the tapered portion of the needle does not come into contact with the tapered section of the in-port path. Therefore, unlike conventional needle ports, with the needle ports 22 and 23 according to the present embodiment, the surface of the tapered section will not be scratched, which always assures the liquid-tightness between the needle and the needle port.

In the needle ports 22 and 23 according to the present embodiment, the surface of the tapered section will not be scratched as described above. Nevertheless, the surface of the inlet section may be scratched. However, this will not cause any problems because the inlet section does not affect the liquid-tightness between the needle ports (22 and 23) and the needles (18 and 31).

Thus far, the best mode for carrying out the present invention has been described using an embodiment. However, the present invention is not limited by the embodiment, and may be appropriately changed within the spirit of the present invention.

For example, the needle port of the present embodiment can be applied not only in the preparative separation-purification system described above, but also in various systems, such as a liquid chromatograph apparatus, an auto sampler or other apparatuses, in which a needle is used for providing a liquid to a passage or for changing passages. In particular, it can be applied to an inlet/outlet end of a variety of columns, an injection port, and other similar units provided in such systems.

EXPLANATION OF NUMERALS 11, 12, 13 . . . Container
14, 17 . . . Selector Valve
15 . . . Introduction Passage
16 . . . Supply Pump
18, 31 . . . Needle
19 . . . Dilution Passage
21 . . . Trap Column
22, 23 . . . Needle Port
24 . . . Internal Space
26 . . . Mesh Cap
27 . . . Aperture
29 . . . Cap
31a . . . Body
31b . . . Tapered Portion
31c . . . Path
32 . . . Discharge Passage
33 . . . T-Joint
34 . . . Discharge Nozzle
35 . . . Fraction Collector Head
39 . . . Disposal Port
42 . . . Collection Container
51 . . . Triaxial Drive Mechanism
52 . . . Controller
53 . . . Operation Unit
60 . . . In-Port Path
61 . . . Inlet Section
62 . . . Guide Section
63 . . . Tapered Section
64 . . . Passage Section
65 . . . Mouth

The invention claimed is:
1. A needle port system comprising:
an in-port path; and a needle for inserting into the in-port path, the needle having a tapered portion on an end of a body and a path inside the body through which a liquid passes, wherein the in-port path comprises:
  a) a guide section having an inside diameter which is larger than an outside diameter of the body of the needle;
  b) a passage section having an inside diameter which is smaller than the outside diameter of the body of the needle and larger than a tip diameter of the tapered portion of the needle; and
  c) a tapered section for connecting the guide section and the passage section, the tapered section having a taper angle which is larger than a taper angle of the tapered portion of the needle and half a difference between a largest inside diameter and a smallest inside diameter of the tapered section is smaller than half a difference between the outside diameter of the body of the needle and the tip diameter.

2. The needle port system according to claim 1, wherein a tapered inlet section is provided before the guide section of the in-port path.

\* \* \* \* \*